(12) United States Patent
Schwarz et al.

(10) Patent No.: US 6,753,326 B1
(45) Date of Patent: Jun. 22, 2004

(54) 14, 15-.α.-METHYLENE EQUILENINE DERIVATIVES, METHODS FOR PRODUCING THE SAME AND MEDICAMENTS CONTAINING THEM

(75) Inventors: Sigfrid Schwarz, Jena (DE); Ina Thieme, Graitschen (DE); Bernd Undeutsch, Jena (DE); Guenter Kaufmann, Jena (DE); Wolfgang Roemer, Jena (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/937,723

(22) PCT Filed: Mar. 22, 2000

(86) PCT No.: PCT/EP00/02513
§ 371 (c)(1),
(2), (4) Date: Jan. 28, 2002

(87) PCT Pub. No.: WO00/59922
PCT Pub. Date: Oct. 12, 2000

(30) Foreign Application Priority Data

Mar. 30, 1999 (DE) .......................................... 199 15 576

(51) Int. Cl.[7] ........................ C07J 53/00; A61K 31/565

(52) U.S. Cl. ........................... 514/178; 514/182; 540/8

(58) Field of Search .............................. 540/8; 514/178, 514/182

(56) References Cited

U.S. PATENT DOCUMENTS 5,318,987 A    6/1994   Weithmann et al. ......... 514/457

FOREIGN PATENT DOCUMENTS

| EP | 0 436 936 A2 | 7/1991 |
| EP | 0 753 300 A  | 1/1997 |
| WO | 95 13076 A   | 5/1995 |
| WO | 98 25626 A   | 6/1998 |

OTHER PUBLICATIONS

Damasio, Alzheimer's Disease and Related Dementias, Cecil Textbook of Medicine, 20th Edition, vol. 2, pp. 1992–1996, 1996.*
Layzer, Degenerative Disease of the Nervous System, Cecil Textbook of Medicine, 20th Edition, vol. 2, pp. 2050–2057, 1996.*
Bhavnani et al., PubMed Abstract (J. Soc. Gynecol. Investig. 9(2):102–10), 2002.*
Gilgun–Sherki et al., PubMed Abstract (Neuropharmacology 40(8):959–75), 2001.*
Branisteanu et al., PubMed Abstract (Rev. Med. Chir. Soc. Med. Nat. lasi. 101(1–2):59–62), 1997.*
Kuenzer, H., et al: " A Concise Total Synthesis of . . . " Tetrahedron Lett, 1994, 35 (15), 2329–30, p. 2329.

Romer W., et al: "Novel @? and their Radical Scavenging Effects, . . . ", Steroids:Structure, Function, and Regulation, US, Elsevier Science Publishers, NY, NY, BD. 62, NR. 3, Mar. 1, 1997, pp. 304–310.
Roemer W et al: "Scavestrogen Sulfamates . . . ", Canadian Journal of Physiology and Pharmacology, CA, Ottawa, Ont, BD. 75, NR. 2, 1998, pp. 99–109.
N. Koizumi et al: "Antiandrogen, IV . . . " Chemical and Pharmaceutical Bulletin, BD. 44, NR. 11, Nov. 1996, pp. 2162–2164.
K. Shibata et al: "Antiandrogen. I . . . " Chemical and Pharmaceutical Bulletin, BD. 40, NR. 4, Apr. 1992, pp. 935–941.
The Solid–Gas Chlorination and . . . by Douglas G. Naae, Department of Chemistry, University of Kentucky, in Tetrahedron Letter No. 32, pp. 2761–2764, 1976. Pergamon Press, Printed in Great Britain.
"Steroid Hormones" By A. J. Birch et al, in Aust. J. Chem., 1970, 23, pp. 547–552.
"Total Synthesis of Steroids . . . " by A. R. Daniewski et al, in J. Org. Chem., vol. 39, No. 15, 1974, pp. 2192–2196.
"A New Synthesis of 3OMethoxy . . . " by D.K. Banerjes et al, in Tetrahedron Letter No. 4, pp. 479–481, 1968. Pergamon Press, Printed in Great Britain.
"Synthesis of 14,17A–Ethano . . . " by H. Kunzer et al, in Tetrahedron Letters, vol. 35, No. 46, pp. 8599–8600, 1994 Pregamon Press, Printed in Great Britain.
"A Concise Total Synthesis of . . . " by H. Kunzer et al, in Tetrahedron Letters, vol. 35, No. 15, pp. 2329–2330, 1994 Pregamon Press, Printed in Great Britain.
"Diphosphorus Tetraiodide as a Reagent for Converting Epoxides . . . " by Hitomi Suzuki et al, in Synthesis, Communications, Dec. 1978, pp. 905–908.

(List continued on next page.)

*Primary Examiner*—Deepak Rao
(74) *Attorney, Agent, or Firm*—Michael J. Striker

(57) ABSTRACT

Described are novel equilenin derivatives of general formula I

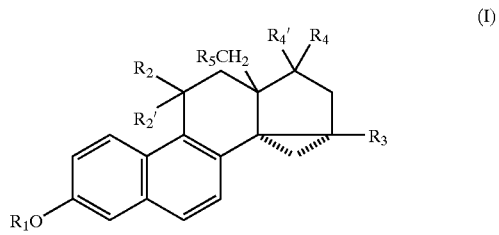

methods for producing the same and medicaments containing these compounds.

The new compounds have antioxidative activity and are usable for geroprophylaxis in women and men.

8 Claims, No Drawings

OTHER PUBLICATIONS

"Photolyse D'Oxazirdines, Facturs . . . " by Esther Oliveros et al, in Nouveau Journal De Chemie, vol. 3, N. 12, 1979, pp. 739–753.

"Diphosphorus Tetraiodide . . . " by M. Lauwers et al, in Tetrahedron Letters, No. 20, pp. 1801–1804, Pergamon Press, Printed in Great Britain, 1979.

"X–Ray Structure Analysis of Iodo . . . " by Pier Luigi Orioli et al, in J.C.S. Chem. Comm, 1975, pp. 229–230.

Hevl. Chim. Acta 11, pp. 106–108, 1928.

Carl Mannich and Martin Dannehl: "Uber Die Bildung Eines . . . " in Bericht 71, NR. Sep. 1938, pp. 1899–1902.

Ferdinand Bohlmann: "Reaktionen Mit Lithiumaluminium . . . " Jahrgang 85, NR. 5, 1952. pp. 386–388.

Richard Kuhn Und Karl Ludwig Scholler: "Ueber Kumulene VI . . . ", in Jahrgang 87, NR. 4, 1954, pp. 598–610.

"Synthesis of Buta –1,2,3–Trienes . . . " by Geirge R. Newkome et al, in J.C.S. Chem.Comm., 1975, pp. 885–886.

* cited by examiner

14,15-α-METHYLENE EQUILENINE DERIVATIVES, METHODS FOR PRODUCING THE SAME AND MEDICAMENTS CONTAINING THEM

BACKGROUND OF THE INVENTION

1. Field of the Invention

The present invention relates to novel equilenin derivatives, methods for producing the same and medicaments containing them.

2. Description of the Related Art

Equilenin itself is an estrogenic steroid obtainable from the urine of pregnant mares.

The novel equilenin derivatives of the invention have an oxygen function on carbon atom 11 and an α-methylene bridge between carbon atoms 14 and 15. Equilenin derivatives with an oxygen function on carbon atom 11 are known. Thus, the racemic 11-oxoequilenin methyl ether was obtained by total synthesis [Tetrahedron Lett. 2763 (1967); Austr. J. Chem. 23, 547 (1970); J. Org. Chem. 39, 2193 (1974)]. A total synthetic route was also used to obtain racemic 11-oxo-3-methoxyestra-1,3,5(10),-6,8,14-hexaen-17β-ylcarboxylic acid [Tetrahedron Lett. 479 (1968)]. 14α,17α-Bridged equilenin derivatives with an 11-oxygen function were obtained by partial synthesis. The introduction of the 11-oxygen function into the molecule was achieved with Ce(IV) ammonium nitrate [Tetrahedron Lett. 35, 8599 (1994)]. Equilenin derivatives with an α- or β-methylene bridge between carbon atoms 14 and 15 have also been prepared by partial synthesis whereby the B ring was dehydrogenated with dichlorodicyanobenzoquinone (DDQ) [Tetrahedron Lett. 35, 2329 (1994)].

SUMMARY OF THE INVENTION

The object of the present invention is to provide novel equilenin derivatives and a method for producing the same.

According to the invention, this objective is attained by forming equilenin derivatives of general formula (I)

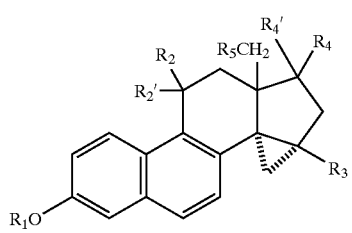

wherein
- $R_1$ denotes a hydrogen atom, a $C_1$–$C_5$-alkyl group, a $C_1$–$C_5$-acyl group or a benzoyl group,
- $R_2$ denotes a hydrogen atom and $R'_2$ denotes a fluorine atom, a hydroxyl group or a $C_1$–$C_5$-acyloxy group or $R_2$ and $R'_2$ together denote an oxo group,
- $R_3$ denotes a hydrogen atom or a methyl group,
- $R_4$ denotes a hydrogen atom and $R'_4$ denotes a hydroxyl group or a $C_1$–$C_{11}$-acyloxy group or $R_4$ and $R'_4$ together denote an oxo group, a methylene group, a halomethylene group or a dihalomethylene group and
- $R_5$ denotes a hydrogen atom or a methyl group.

According to the invention, $R_6$ is preferably a hydrogen atom.

According to the invention, particularly preferred equilenin derivatives are for example:

1) 14α,15α-methylenestra-1,3,5(10),6,8-pentaene-3,11β,17β-triol,
2) 11β,17β-dihydroxy-14α,15α-methylenestra-1,3,5(10),6,8-pentaen-3-yl benzoate,
3) 11β,17β-dihydroxy-14α,15α-methylenestra-1,3,5(10),6,8-pentaen-3-yl propionate,
4) 3,11β-dihydroxy-14α,15α-methylenestra-1,3,5(10),6,8-pentaen-17β-yl decanoate,
5) 3,11β-dihydroxy-14α,15α-methylenestra-1,3,5(10),6,8-pentaen-17-one,
6) 3-methoxy-14α,15α-methylenestra-1,3,5(10),6,8-pentaen-11α,17β-diyl diacetate,
7) 15β-methyl-14α,15α-methylenestra-1,3,5(10),6,8-pentaene-3,11β,17β-triol,
8) 11β-fluoro-14α,15α-methylenestra-1,3,5(10),6,8-pentaene-3,17β-diol,
9) 3,17β-dihydroxy-14α,15α-methylene-1,3,5(10),6,8-pentaen-11-one,
10) 3-methoxy-14α,15α-methylenestra-1,3,5(10),6,8-pentaen-11α,17α-diyl diacetate,
11) 3-methoxy-14α,15α-methylene-11-oxoestra-1,3,5(10),6,8-pentaen-17α-yl acetate,
12) 11β-hydroxy-17,17-difluoromethylene-14α,15α-methylenestra-1,3,5(10),6,8-pentaen-3-yl benzoate, and
13) 14α,15α-17,17-bis-methylenestra-1,3,5(10),6,8-pentaene-3,11α-diol.

For purposes of the present invention, "$C_1$–$C_6$-alkyl" means a branched or straight-chain alkyl group. Examples are the methyl, ethyl, n-propyl, isopropyl, n-butyl, isobutyl or tert.butyl, n-pentyl or isopentyl groups.

For purposes of the present patent application, "$C_{1-6}$-acyl or $C_{1-11}$-acyl" means a radical of a straight-chain or branched alkanecarboxylic acid with 1 to 5 or with 1 to 11 carbon atoms, for example a radical of formic, acetic, propionic, butanoic, isobutanoic, heptanoic or undecanoic acid.

For purposes of the present invention, "halogen" means an atom of fluorine, chlorine, bromine or iodine.

The equilenin derivatives of the invention are new. Thus far, they have neither been prepared nor have their properties been described. The equilenin derivatives of the invention exhibit antioxidative activity and minor systemic hormonal action. The antioxidative activity was determined by, among other things, inhibition of iron(II)-catalyzed lipid peroxidation in synaptosomal membrane fractions of rats, by inhibition of copper(II) sulfate-induced LDL cholesterol oxidation and by inhibition of xanthine oxidase and of various other monooxygenases. The systemic estrogen action was evaluated by the Allen-Doisy test in rats. The spectrum of activity of the equilenin derivatives of the invention makes them potentially suitable for therapeutic use in all those cases in which oxygen radicals are in a causal relationship with diseases of organs or tissues, for example in brain or spinal column injuries, states of shock, emphysema, acute respiratory distress syndrome (ARDS), ageing processes, tissue injuries after a myocardial infarction, injuries caused by intoxication or irradiation, burns and transplantation-related immune reactions, such as organ injuries in the reperfusion phase following transplantations, in spinal trauma, stroke, arteriosclerosis, ischemia, chronic-degenerative diseases of the CNS, senile dementia of the Alzheimer type (SDAT), asthma, muscular dystrophy and degenerative neurological diseases, among others, in the form of CNS intoxication or degeneration states. A preferred field of application is geroprophylaxis in women and—because the compounds of the invention exert only minor feminization action—also in men.

The compounds of the invention can be administered orally as well as parenterally. For oral administration, pro-drugs in the form of carboxylate esters are particularly advantageous, because they provide active substance levels that remain constant for a long time.

Another object of the present invention is a method for producing the equilenin derivatives of the invention of general formula (I)

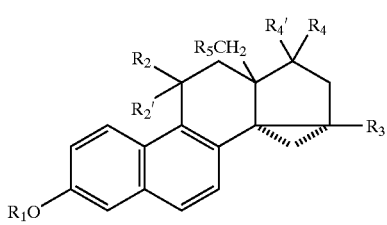

wherein $R_1$, $R_2$, $R_2'$, $R_3$, $R_4$, $R_4'$ and $R_6$ have the afore-indicated meaning, by making a compound of general formula (II)

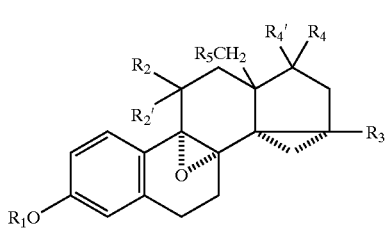

wherein $R_1$, $R_2$, $R_2'$, $R_3$, $R_4$, $R_4'$ and $R_5$ have the afore-indicated meaning, react with diphosphorus tetraiodide in the presence of pyridine, and then converting the resulting compound into a compound of general formula (I) in a manner which in itself is known.

It is known that diphosphorus tetraiodide reacts with epoxides and alcohols. Thus, epoxides can be reduced to olefins with diphosphorus tetraiodide [Synthesis 905 (1978); Nouv. J. Chem. 3, 745 (1979)]. Alcohols react with diphosphorus tetraiodide forming iodides [Tetrahedron Letters 1801 (1979); J.C.S. Chem. Commun. 229 (1983)] or with elimination to give olefins [Helv. Chim. Acta 11, 106 (1928)] or to give cumulenes. [Ber. 71, 1899 (1938)]; ibid. 85, 386 (1952); ibid. 87, 598 (1954); J.C.S. Chem. Commun. 885 (1975)]. An outstanding feature of the method of the invention is that the action of diphosphorus tetraiodide on compounds of general formula (II) eliminates the 8,9-oxido group and at the same time introduces an additional double bond between carbon atoms 6 and 7. In this manner, it is possible to produce the equilenin derivatives of the invention having general formula (I) from compounds of general formula II in one step, and to avoid an additional reaction step to introduce the 6,7-double bond [Tetrahedron Letters 35, 2329 (1994)]. Another outstanding feature of the method of the invention—provided that compounds of general formula 11 are used wherein $R_2$ denotes hydrogen and $R_2'$ stands for a hydroxyl group— is that neither elimination of the unprotected hydroxyl group to the corresponding olefin nor substitution of the hydroxyl group with iodine takes place. The course and the high selectivity of the method of the invention are surprising and could not have been predicted by someone skilled in the art.

Compounds of general formula II can be obtained from compounds of general formula III, wherein $R_1$ and $R_3$ to $R_5$ have the same meaning as indicated for the compounds of formula II, by treating said compounds of formula III with excess peroxycarboxylic acid

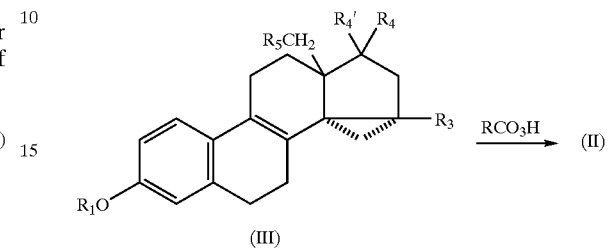

Optionally, the equilenin structure of the derivatives obtained according to the invention can be further modified by methods that in themselves are known. For example, it is possible to subject compounds of general formula I, wherein $R_2'$ denotes an α-hydroxyl group and $R_2$ a β-hydrogen, to oxidation with activated dimethyl sulfoxide in a known manner to form the corresponding 11-oxo compounds which can then be reduced with a complex metal hydride to form the corresponding 11β-hydroxy derivatives. Alternatively, the reaction of compounds of general formula I, wherein $R_2'$ denotes an α-hydroxyl group and $R_2$ a β-hydrogen, with diethylaminosulfur trifluoride (DAST) gives compounds with an 11β-fluoro group. Compounds of general formula I, wherein $R_4'$ denotes a $C_1$–$C_6$-alkyl group, can be converted into the free phenols with boron tribromide or diisobutyla-luminum hydride in a manner which in itself is known. Compounds of general formula I, wherein $R_4'$ denotes an α-hydroxyl group and $R_4$ a β-hydrogen, can be oxidized with activated dimethyl sulfoxide in a manner which in itself is known to give the corresponding 17-oxosteroids, which upon reduction with borane or an oxazaborolidine afford 17β-hydroxy compounds.

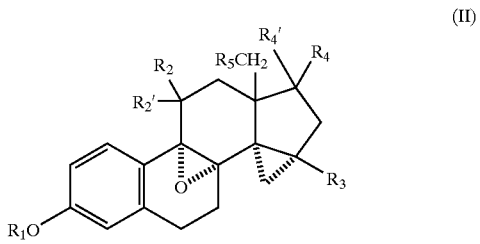

The cyclopropano steroids of general formula II wherein $R_1$ denotes a hydrogen atom, a $C_1$–$C_5$-alkyl group, a $C_1$–$C_5$-acyl group or a benzoyl group, $R_2$ denotes a hydrogen atom and $R'_2$ denotes a fluorine atom, a hydroxyl group or a $C_1$–$C_5$-acyloxy group or $R_2$ and $R'_2$ together denote an oxo group, $R_3$ denotes a hydrogen atom or a methyl group, $R_4$ denotes a hydrogen atom and $R'_4$ denotes a hydroxyl group or a $C_1$–$C_{11}$-acyloxy group or $R_4$ and $R'_4$ together denote an oxo group, a methylene group, a halomethylene group or a dihalomethylene group and $R_5$ denotes a hydrogen atom or a methyl group, are new and have previously not been described.

Particularly preferred, are, for example, the following cyclopropano steroids:
1) 11α-hydroxy-3-methoxy-14α,15α-methylene-8α,9α-oxidoestra-1,3,5(10)-trien-17α-yl acetate,
2) 3-methoxy-14α,15α-methylene-8α,9α-oxidoestra-1,3,5(10)-trien-11α,17α-diyl diacetate and
3) 3-methoxy-11α-hydroxy-8α,9α-oxido-14α,15α-methylenestra-1,3,5(10)-trien-17β-yl acetate.

These compounds represent novel intermediates for obtaining the equilenin derivatives of the invention and thus constitute a further object of the present invention.

The object of the present invention are also medicaments for oral, transdermal, rectal, subcutaneous, intravenous or intramuscular administration which contain a compound of general formula I as the active ingredient besides common carriers or diluents.

The medicaments of the invention are prepared in the known manner with an appropriate active substance content using common solid or liquid carriers or diluents and the commonly employed pharmaceutical auxiliary agents, depending on the route of administration desired. The preferred preparations are dosage forms suitable for oral administration. Such dosage forms are, for example, tablets, film-coated tablets, sugar-coated tablets, capsules, pills, powders, solutions, suspensions or depot forms.

Naturally, parenteral preparations such as solutions for injection are also suitable. Other suitable preparations are, for example, suppositories.

Accordingly, tablets can be obtained, for example, by mixing the active substance with known auxiliary agents, for example with an inert diluent such as dextrose, sugar, sorbitol, mannitol, polyvinylpyrrolidone, a disintegrant such as corn starch or alginic acid, a binder such as starch or gelatin, a lubricant such as magnesium stearate or talc and/or an agent for producing a depot effect, such as carboxypolymethylene, carboxymethylcellulose, cellulose acetate phthalate or polyvinyl acetate. The tablets can consist of several layers.

Coated tablets can be prepared by coating cores, prepared in the same manner as the tablets, with substances commonly used for tablet coating, for example polyvinylpyrrolidone, shellac, gum arabic, talc, titanium dioxide or sugar. The coating of the coated tablet can also consist of several layers obtained with the aid of auxiliary agents mentioned hereinabove in relation to the tablets.

Solutions or suspensions comprising the active substance of the invention can additionally contain a taste-improving agent such as saccharin, cyclamate or sugar, and also, for example, a flavoring agent such as vanillin or orange extract. They can also contain a suspension aid such as sodium carboxymethylcellulose or a preservative such as a p-hydroxybenzoate. Capsules containing an active substance can be prepared, for example, by mixing the active substance with an inert carrier, such as lactose or sorbitol, and encapsulating the mixture in gelatin capsules.

Suitable suppositories can be prepared, for example, by mixing the active substance with a carrier suitable for this purpose, for example with a neutral fat or polyethylene glycol or a derivative thereof.

A suitable dosage form is, for example, active substance-containing adhesive tape. Such systems are known.

The following examples will explain the invention.

EXAMPLE 1

11α-Hydroxy-3-methoxy-14α,15α-methylene-8α,9α-oxidoestra-1,3,5(10)-trien-17α-yl acetate from 3-methoxy-14α,15α-methylenestra-1,3,5(10),8-tetraen-17α-yl acetate Peroxyacetic acid (32%, 5.5 mL) was added at room temperature to a solution of the tetraene steroid (3.5 g) in dichloromethane (120 mL). The reaction mixture was allowed to stand overnight at room temperature. The solution was then treated in succession with aqueous sodium thiosulfate solution (20%), saturated aqueous sodium hydrogen carbonate solution and water. The organic phase was dried over magnesium sulfate and concentrated under vacuum. The residue was subjected to flash chromatography on silica gel (eluent: cyclohexane-ethyl acetate, 3:2 v/v). Crystallization from acetone/n-hexane gave the title compound.

M.p. 159–162.5° C. $^1$H-NMR (CDCl$_3$/TMS$^1$): 7.80 (d, J=8.8 Hz, H-1), 6.79 (dd, J=8.8, 2.8 Hz, H-2), 6.65 (d, J=2.8 Hz, H-4), 4.93 (q, J=7.9 Hz, H-11), 4.78 (d, J=5.9 Hz, H-17), 3.80 (s, —OCH$_3$), 2.03 (s, —OOC—CH$_3$), 1.11 (dd, J=5.4, 3.2 Hz, 14, 15-CH$_2$—), 0.88 (s, H-18), 0.69 (ddd, J=6.6, 5.4, 1.7 Hz, 14, 15-CH$_2$—). MS (m/z): 354 (M$^+$), 336, 294, 277, 261.

EXAMPLE 2

3-Methoxy-14α,15α-methylene-8α,9α-oxidoestra-1,3,5(10)-trien-11α,17α-diyl diacetate from 11α-hydroxy-3-methoxy-14α,15α-methylene-8α,9α-oxidoestra-1,3,5(10)-trien-17α-yl acetate Acetic anhydride (4 mL) and dimethylaminopyridine (0.04 g) were added at room temperature to a solution of the 11α-hydroxy steroid (0.4 g) in pyridine (4 mL). The mixture was stirred at room temperature for 3 hours after which it was poured into ice water. The resulting precipitate was filtered off, washed neutral with water and air-dried. Flash chromatography on silica gel (eluent: cyclohexane-ethyl acetate, 7:3 v/v) gave the title compound.

M.p. 151–154° C. $^1$H-NMR CCDCl$_3$/TMS): 7.80 (d, J=8.8 Hz, H-1), 6.79 (dd, J=8.8, 2.8 Hz, H-2), 6.65 (d, J=2.8 Hz, H-4), 4.93 (q, J=7.9 Hz, H-11), 4.78 (d, J=5.9 Hz, H-17), 3.80 (s, —OCH$_3$), 2.03 (s, —OOC—CH$_3$), 1.11 (dd, J=5.4, 3.2 Hz, 14, 15-CH$_2$—), 0.88 (s, H-18), 0.69 (ddd, J=6.6, 5.4, 1.7 Hz, 14, 15—CH$_2$—). MS (m/z): 354 (M$^+$) 336, 294, 277, 261.

[1] TMS=tetramethylsilane—Translator

EXAMPLE 3

3-Methoxy-14α,15α-methylenestra-1,3,5(10),6,8-pentaen-11α,17α-diyl diacetate from 3-methoxy-14α,15α-methylene-8α,9α-oxidoestra-1,3,5(10)-trien-11α,17α-diyl diacetate A solution consisting of the steroid diacetate (0.1 g), chloroform (2.4 mL) and pyridine (0.24 mL) was added dropwise to a stirred suspension of diphosphorus tetraiodide (0.14 g) in chloroform (2.4 mL) under argon protection. The mixture was then heated at reflux for 13 hours with agitation. Water was added, the organic phase was separated, and the aqueous phase was extracted exhaustively with chloroform. The combined organic phases were washed in succession with hydrochloric acid (1 N), water, saturated aqueous sodium hydrogen carbonate solution and saturated aqueous sodium chloride solution and then dried over magnesium sulfate and concentrated under vacuum. The residue was subjected to flash chromatography which gave the title compound.

$^1$H-NMR (CDCl$_3$/TMS): 7.66 (d, J=8.8 Hz, H-6,7), 7.58 (d, J=9.5 Hz, H-1), 7.17 (dd, J=9.5, 2.8 Hz, H-2), 7.13 (d, J=2.8 Hz, H-4), 6.85 (d, J=8.8 Hz, H-6,7), 6.78 (q, J=8.1 Hz, H-11), 4.98 (d, J=6.1 Hz, H-17), 3.92 (s, —OCH$_3$), 2.11 (s, —OOC—CH$_3$), 2.09 (s, —OOC—CH$_3$), 1.46 (dd, J=4.9, 3.2 Hz, 14, 15-CH$_2$—), 0.97 is, H-18), 0.57 (ddd, J=8.2, 4.9, 1.7 Hz, 14, 15—CH$_2$—). MS (m/z): 394 (M$^+$), 334, 274, 259.

EXAMPLE 4

11α-Hydroxy-3-methoxy-14α,15α-methylenestra-1, 3,5(10),6,8-pentaen-17α-yl acetate from 11α-hydroxy-3-methoxy-14α,15α-methylene-8α,9α-oxidoestra-1,3,5(10)-trien-17α-yl acetate As in Example 3, the 11-hydroxy compound was treated with diphosphorus tetraiodide, which gave the title compound.

$^1$H-NMR (CDCl$_3$/TMS): 8.26 (d, J=9.4 Hz, H-1), 7.62 (d, J=8.3 Hz, H-6,7), 7.22 (dd, J=9.4, 2.7 Hz, H-2), 7.12 (d, J 2.7 Hz, H-4), 6.83 (d, J=8.3 Hz, H-6,7), 5.68 (q, J=7.7 Hz, H-11), 4.99 (d, J=6.3 Hz, H-17), 3.92 (s, —OCH$_3$), 2.10 (s, —OOC—CH$_3$), 0.93 (s, H-18), 0.57 (ddd, J=7.6, 4.8, 1.6 Hz, 14, 15—CH$_2$—). MS (m/z): 370 (M$^+$), 353, 310, 292, 277, 267.

What is claimed is:

1. An equilenin derivative of formula I:

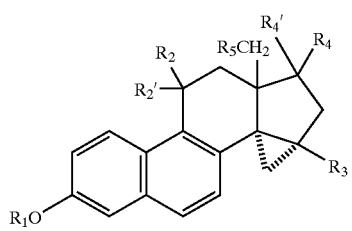

(I)

wherein
- R$_1$ denotes a hydrogen atom, a C$_1$–C$_5$-alkyl group, a C$_1$–C$_5$-acyl group or a benzoyl group,
- R$_2$ denotes a hydrogen atom and R'$_2$ denotes a fluorine atom, a hydroxyl group or a C$_1$–C$_5$-acyloxy group or R$_2$ and R'$_2$ together denote an oxo group,
- R$_3$ denotes hydrogen atom or a methyl group,
- R$_4$ denotes a hydrogen atom and R'$_4$ denotes a hydroxyl group or a C$_1$–C$_{11}$-acyloxy group or R$_4$ and R'$_4$ together denote an oxo group, a methylene group, a halomethylene group or a dihalomethylene group and
- R$_5$ denotes a hydrogen atom or a methyl group.

2. The equilenin derivative as defined in claim 1, wherein said R$_5$ is said hydrogen.

3. An equilenin derivative selected from the group consisting of
- 14α,15α-methylenestra-1,3,5(10),6,8-pentaene-3,11β,17β-triol,
- 11β,17β-dihydroxy-14α,15α-methylenestra-1,3,5(10),6,8-pentaene-3-yl benzoate,
- 11β,17β-dihydroxy-14α,15α-methylenestra-1,3,5(10),6,8-pentaene-3-yl proplonate,
- 3,11β-dihydroxy-14α,15α-methylenestra-1,3,5(10),6,8-pentaene-17β-yl decanoate,
- 3,11β-dihydroxy-14α,15α-methylenestra-1,3,5(10),6,8-pentaene-17-one,
- 3-methoxy-14α,15α-methylenestra-1,3,5(10),6,8-pentaene-11α,17β-diyl diacetate,
- 15β-methyl-14α,15α-methylenestra-1,3,5(10),6,8-pentaene-3,11β,17β-triol;
- 11β-fluoro-14α,15α-methylenestra-1,3,5(10),6,8-pentaene-3,17β-diol,
- 3,17β-dihydroxy-14α,15α-methylenestra-1,3,5(10),6,8-pentaene-11-one,
- 3-methoxy-14α,15α-methylenestra-1,3,5(10),6,8-pentaene-11α,17α-diyl diacetate,
- 3-methoxy-14α,15α-methylen-11-oxoestra-1,3,5(10),6,8-pentaene-17α-yl acetate,
- 11β-hydroxy-17,17-difluoromethylene-14α,15α-methylenestra-1,3,5(10),6,8-pentaene-3-yl benzoate and
- 14α,15α-methylene-17,17-bis-methyleneestra-1,3,5(10),6,8-pentaene-3,11α-diol.

4. A method of making an equilenin derivative of formula I:

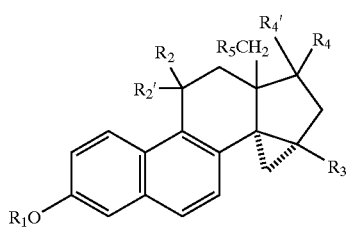

(I)

wherein
- R$_1$ denotes a hydrogen atom, a C$_1$–C$_5$-alkyl group, a C$_1$–C$_5$-acyl group or a benzoyl group,
- R$_2$ denotes a hydrogen atom and R'$_2$ denotes a fluorine atom, a hydroxyl group or a C$_1$–C$_5$-acyloxy group or R$_2$ and R'$_2$ together denote an oxo group,
- R$_3$ denotes a hydrogen atom or a methyl group,
- R$_4$ denotes a hydrogen atom and R'$_4$ denotes a hydroxyl group or a C$_1$–C$_{11}$-acyloxy group or R$_4$ and R'$_4$ together denote an oxo group, a methylene group, a halomethylene group or a dihalomethylene group and
- R$_5$ denotes a hydrogen atom or a methyl group;

said method comprising the steps of:
  a) reacting diphosphorus tetraiodide in the presence of pyridine with a compound to formula II:

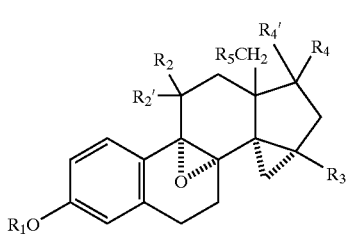

(II)

to form an intermediate product, and
  b) converting the intermediate product to said equilenin derivative of said formula I.

5. A pharmaceutical composition comprising at least one member selected from the group consisting of pharmaceutically compatible agents and carriers; and at least one equilenin derivative of formula I:

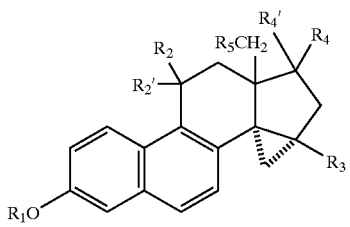

(I)

wherein
- $R_1$ denotes a hydrogen atom, a $C_1$–$C_5$-alkyl group, a $C_1$–$C_5$-acyl group or a benzoyl group,
- $R_2$ denotes a hydrogen atom and $R'_2$ denotes a fluorine atom, a hydroxyl group or a $C_1$–$C_5$-acyloxy group or $R_2$ and $R'_2$ together denote an oxo group,
- $R_3$ denotes a hydrogen atom or a methyl group,
- $R_4$ denotes a hydrogen atom and $R'_4$ denotes a hydroxyl group or a $C_1$–$C_{11}$-acyloxy group or $R_4$ and $R'_4$ together denote an oxo group, a methylene group, a halomethylene group or a dihalomethylene group and
- $R_5$ denotes a hydrogen atom or a methyl group.

6. A pharmaceutical composition comprising
at least one member selected from the group consisting of pharmaceutically compatible agents and carriers; and
at least one equilenin derivative selected from the group consisting of:
14α,15α-methylenestra-1,3,5(10),6,8-pentaene-3,11β,17β-triol,
11,17β-dihydroxy-14α,15α-methylenestra-1,3,5(10),6,8-pentaene-3-yl benzoate,
11β,17β-dihydroxy-14α,15α-methylenestra-1,3,5(10),6,8-pentaene-3-yl propionate,
3,11β-dihydroxy-14α,15α-methylenestra-1,3,5(10),6,8-pentaene-17β-yl decanoate,
3,11β-dihydroxy-14α,15α-methylenestra-1,3,5(10),6,8-pentaene-17-one,
3-methoxy-14α,15α-methylenestra-1,3,5(10),6,8-pentaene-11α,17β-diyl diacetate,
15β-methyl-14α,15α-methylenestra-1,3,5(10),6,8-pentaene-3,11β,17β-triol,
11β-fluoro-14α,15α-methylenestra-1,3,5(10),6,8-pentaene-3,17β-diol,
3,17β-dihydroxy14α,15α-methylenestra-1,3,5(10),6,8-pentaene-11-one,
3-methoxy-14α,15α-methylenestra-1,3,5(10),6,8-pentaene-11α,17α-diyl diacetate,
3-methoxy-14α,15α-methylen-11-oxoestra-1,3,5(10),6,8-pentaene-17α-yl acetate,
11β-hydroxy-17,17-difluoromethylene-14α,15α-methylenestra-1,3,5(10),6,8-pentaene-3yl benzoate and
14α,15α-methylene-17,17-bis-methyleneestra-1,3,5(10),6,8-pentaene-3,11α-diol.

7. A cyclopropano steroid of formula II:

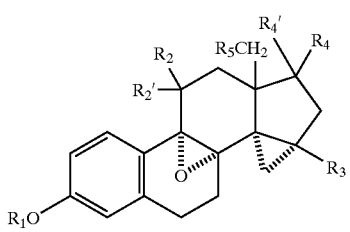

(II)

wherein
- $R_1$ denotes a hydrogen atom, a $C_1$–$C_5$-alkyl group, a $C_1$–$C_5$-acyl group or a benzoyl group,
- $R_2$ denotes a hydrogen atom and $R'_2$ denotes a fluorine atom, a hydroxyl group or a $C_1$–$C_5$-acyloxy group or $R_2$ and $R'_2$ together denote an oxo group,
- $R_3$ denotes a hydrogen atom or a methyl group,
- $R_4$ denotes a hydrogen atom and $R'_4$ denotes a hydroxyl group or a $C_1$–$C_{11}$-acyloxy group or $R_4$ and $R'_4$ together denote an oxo group, a methylene group, a halomethylene group or a dihalomethylene group and
- $R_5$ denotes a hydrogen atom or a methyl group.

8. A cyclopropano steroid selected from the group consisting of
11α-hydroxy-3-methoxy-14α,15α-methylene-8α,9α-oxidoestra-1,3,5(10)-trien-17α-yl acetate, 3-methoxy-14α,15α-methylene-8α,9α-oxidoestra-1,3,5(10)-trien-11α,17α-diyl diacetate and
3-methoxy-11α-hydroxy-8α,9α-oxido-14α,15α-methylenestra-1,3,5(10)-trien-17β-yl acetate.

* * * * *